(12) United States Patent
Miller

(10) Patent No.: US 8,937,194 B2
(45) Date of Patent: *Jan. 20, 2015

(54) TOPICAL COMPOSITIONS CONTAINING NITRO FATTY ACIDS

(75) Inventor: Raymond A. Miller, Magnolia, OH (US)

(73) Assignee: Nitromega Corp., Pittsburgh, PA (US)

( * ) Notice: Subject to any disclaimer, the term of this patent is extended or adjusted under 35 U.S.C. 154(b) by 62 days.

This patent is subject to a terminal disclaimer.

(21) Appl. No.: 13/174,206

(22) Filed: Jun. 30, 2011

(65) Prior Publication Data

US 2011/0256247 A1    Oct. 20, 2011

Related U.S. Application Data

(63) Continuation-in-part of application No. 12/651,079, filed on Dec. 31, 2009.

(60) Provisional application No. 61/141,844, filed on Dec. 31, 2008.

(51) Int. Cl.

| | |
|---|---|
| *A61K 31/04* | (2006.01) |
| *A61K 31/201* | (2006.01) |
| *A23L 1/00* | (2006.01) |
| *A23L 1/30* | (2006.01) |
| *A23L 1/302* | (2006.01) |
| *A61K 9/00* | (2006.01) |
| *A61K 8/36* | (2006.01) |
| *A61K 8/40* | (2006.01) |
| *A61Q 19/00* | (2006.01) |
| *A61K 8/11* | (2006.01) |

(52) U.S. Cl.
CPC ............... *A23L 1/0029* (2013.01); *A23L 1/30* (2013.01); *A23L 1/3008* (2013.01); *A23L 1/302* (2013.01); *A61K 9/0014* (2013.01); *A61K 8/361* (2013.01); *A61K 8/40* (2013.01); *A61Q 19/00* (2013.01); *A61K 8/11* (2013.01); *A61K 2800/92* (2013.01)
USPC .......................................... 554/111; 514/560

(58) Field of Classification Search
CPC ............................. A61K 31/201; A61K 31/04
See application file for complete search history.

(56) References Cited

U.S. PATENT DOCUMENTS

| | | | | |
|---|---|---|---|---|
| 5,443,844 | A * | 8/1995 | McDaniel | 424/484 |
| 6,924,309 | B2 * | 8/2005 | Ferrante et al. | 514/560 |
| 2007/0232579 | A1 * | 10/2007 | Freeman et al. | 514/178 |

OTHER PUBLICATIONS

Zouboulis, Christos C. "Is acne vulgaris a genuine inflammatory disease?." Dermatology 203.4 (2001): 277-279.*
Farris, Patricia K. "Topical vitamin C: a useful agent for treating photoaging and other dermatologic conditions." Dermatologic surgery 31.s1 (2005): 814-818.*
Napolitano, Alessandra, et al. "Acid-induced structural modifications of unsaturated fatty acids and phenolic olive oil constituents by nitrite ions: a chemical assessment." Chemical research in toxicology 17.10 (2004): 1329-1337.*
Weldon, Sinéad M., et al. "Docosahexaenoic acid induces an anti-inflammatory profile in lipopolysaccharide-stimulated human THP-1 macrophages more effectively than eicosapentaenoic acid." The Journal of nutritional biochemistry 18.4 (2007): 250-258.*
Pischon, Tobias, et al. "Habitual dietary intake of n-3 and n-6 fatty acids in relation to inflammatory markers among US men and women." Circulation 108.2 (2003): 155-160.*

* cited by examiner

*Primary Examiner* — David J Blanchard
*Assistant Examiner* — Peter Anthopolos
(74) *Attorney, Agent, or Firm* — Dureska, Kennedy & Moore, L.L.C.; David P. Dureska; Brent L. Moore

(57) ABSTRACT

Activated fatty acids, topical compositions including activated fatty acids and methods for using activated fatty acids to treat a variety of diseases.

6 Claims, 1 Drawing Sheet

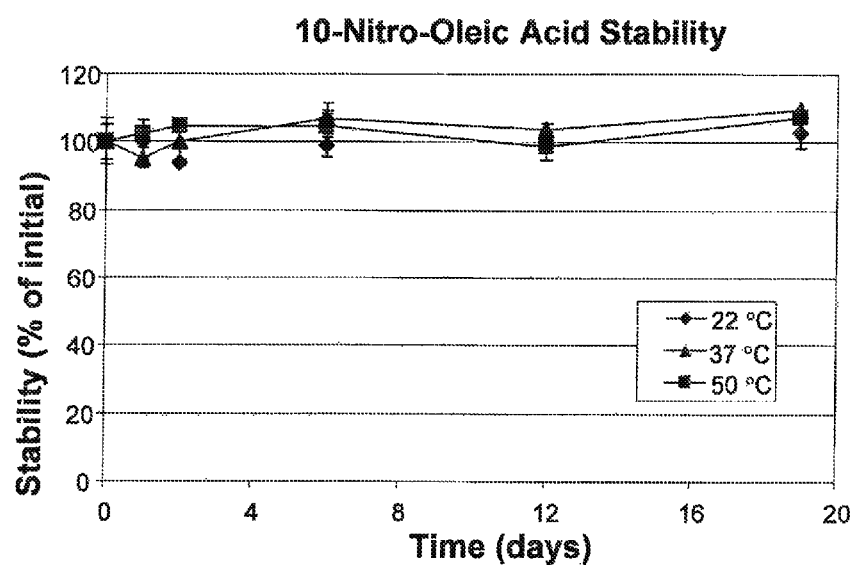

TOPICAL COMPOSITIONS CONTAINING NITRO FATTY ACIDS

CROSS-REFERENCE TO RELATED APPLICATION

This application is a continuation-in-part of U.S. patent application Ser. No. 12/651,079, filed on Dec. 31, 2009, which claims the benefit of U.S. Provisional Application No. 61/141,844, filed on Dec. 31, 2008.

SUMMARY

Embodiments of the invention presented herein are directed to nutritional or dietary supplements, topical formulation, such as salves and lotions, and other nutraceutical compositions that include one or more activated fatty acids such as for example, nitro fatty acids.

In some embodiments, the nutraceutical supplements and topical formulations may include one or more nutraceutical other than nitro fatty acids such as rice bran oil, enzyme-treated stabilized rice bran, a solubilized fraction of rice bran oil, and derivatives thereof, glucosamine derivatives, methylsulfonylmethane, yucca concentrate, grape seed extract, beta-carotene, ephedra, ginko biloba, goldenseal, valerian, ginseng, and echinacea. The activated fatty acids may be isolated from a natural source such as fish oil and may be derived from omega-3 fatty acids, linoleic acid, α-linoleic acid, oleic acid, eicosapentaenoic acid, docosahexaenoic acid or a derivative or combination thereof. In particular embodiment, the nutraceuticals may further include non-nitrated fatty acids.

For topical formulations the nutraceutical may include a dermatalogically acceptable vehicle, and in certain embodiments other nutraceuticals such as, for example, hyaluronic acid, chondroitin sulphate, collagen glucosamine, keratan sulphate, dermatan sulphate, vitamin C, green tea extract, shea butter, grape-seed extract, aloe extract, or mixtures thereof.

Some embodiments of the invention are directed to the selection, formulation, and use of compounds which act with a protective response to prevent and attenuate inflammation to provide a therapeutic effect in their control of the pathological inflammation processes, and are also important in providing useful biochemical tools for mechanistic investigation of the enzymes involved.

Some embodiments of the invention are directed to the topical use of nitroalkene compositions, including particularly, nitrilinoleic acid, nitrooleic acid, nitrated species of arachidonic acid and nitrated cholesteryl lineoleate, as lipi signaling mediatos to reduce inflammation and inflammation mediated skin conditions.

Some embodiments of the invention provide therapeutically effective topical compositions of nitroalkene and carrier to prevent, treat, or otherwise improve the skin conditions through topical application.

Some embodiments of the invention provide methods for preventing and/or treating skin damage that comprise applying a composition containing nitroalkene in a dermatologically acceptable carrier to skin.

In accordance with the present invention, topical methods of use of nitroalkenes to prevent or treat rosacea, eczema, psoriasis, xerosis, dermatitis, seborrhea, acne, alopecia, other types of skin inflammation, skin aging, and scarring are disclosed.

The amount of nitroalkene necessary to treat skin or prevent skin damage is not fixed per se and is necessarily dependent upon the amount and identity of any adjunct ingredients in the preparation. In some typical embodiments of the invention, the composition comprises about 0.025% to about 70% by weight nitroalkene in a dermatologically acceptable polymer polyether and/or phosphatidycholine carrier. Optionally, at least one or a mixture of lipoic acid, fatty acid ester of ascorbic acid may be added to the composition.

In some typical embodiments of the invention, the method for preventing and/or treating skin damage comprises applying a composition containing about 0.025% to about 70% by weight of nitroalkene in a dermatologically acceptable carrier. Optionally, at least one or a mixture of lipoic acid or fatty acid ester of ascorbic acid may be added to the composition.

Some embodiments are directed to a dietary supplement including a fatty acid component enriched for one or more activated fatty acids fatty acids and a nutraceutically acceptable excipient. In some embodiments, the activated fatty acid may be derived from an omega-3 fatty acid, an omega-6 fatty acid, an omega-9 fatty acid, and combinations thereof. In other embodiments, the activated fatty acid may be a nitro-fatty acid or a keto-fatty acid, and in particular embodiments, the activated fatty acid may be nitro-linoleic acid, nitro-α-linoleic acid, nitro-γ-linoleic acid, nitro-oleic acid, nitro-eicosapentaenoic acid, nitro-docosahexaenoic acid, keto-linoleic acid, keto-γ-linoleic acid, keto-α-linoleic acid, keto-oleic acid, keto-eicosapentaenoic acid, keto-docosahexaenoic acid or a derivative or combination thereof. In still other embodiments, the dietary supplement may also include one or more of linoleic acid, α-linoleic acid, γ-linoleic acid, oleic acid, eicosapentaenoic acid (EPA), docosahexaenoic acid (DHA), or derivatives thereof. In some embodiment, the dietary supplement may further include one or more nutraceutical selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat gene extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof.

In particular embodiments, the dietary supplement may include a first fatty acid component enriched for one or more activated fatty acid selected from nitro-linoleic acid, keto-linoleic acid, nitro-oleic acid, and keto-oleic acid and a second fatty acid component having one or more non-activated fatty acid selected from linoleic acid, γ-linoleic acid, α-linoleic acid, oleic acid, eicosapentaenoic acid (EPA), docosahexaenoic acid (DHA), or derivatives thereof, and in some embodiments, the dietary supplement may further include vitamin E or a derivative thereof. In other embodiments, the dietary supplement may include one or more secondary agent including but not limited to vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, gugulipds, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote general health.

Various embodiments of the invention are also directed to pharmaceutical composition. In such embodiments, the one or more nitro fatty acids may make up about 10% by weight to about 95% by weight. As above, the pharmaceutical compositions may include one or more nutraceutical other than nitro fatty acids such as, for example, rice bran oil, enzyme-treated stabilized rice bran, a solubilized fraction of rice bran oil, and derivatives thereof, glucosamine derivatives, methylsulfonylmethane, yucca concentrate, grape seed extract, beta-carotene, ephedra, ginko biloba, goldenseal, valerian, ginseng, and echinacea. The activated fatty acid may be derived from an omega-3 fatty acids, omega-6 fatty acids, omega-9 fatty acids, α-linoleic acid, γ-linoleic acid, oleic acid, eicosapentaenoic acid, docosahexaenoic acid or a derivative or combination thereof, and may contain non-activated fatty acids. Such pharmaceutical compositions may be topical compositions, and in some embodiments, the compositions may further include other agents such as solubilizers, stabilizers, colorants, plasticizers diluents, fillers, disintegrants, binders, lubricants, surfactants, hydrophobic vehicles, water soluble vehicles, emulsifiers, buffers, humectants, moisturizers, antioxidants, preservatives or combinations thereof. In still other embodiments, the composition, may further include one or more secondary agents such as, for example, antioxidants, statins, squalene synthesis inhibitors, azetidinone-based compounds, LDL catabolism activators, PPAR antagonists or agonists, antiarrhythmic agent, NSAIDs and nutraceutical equivalents thereof.

Further embodiments are directed to methods for improving the health of an individual by administering to the individual a dietary supplement including a fatty acid component enriched for one or more activated fatty acids fatty acids, and a nutraceutically acceptable excipient. In some embodiments, the dietary supplement may include a first fatty acid component enriched for one or more activated fatty acid selected from nitro-linoleic acid, keto-linoleic acid, nitro-oleic acid, and keto-oleic acid and a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof, and in particular embodiments, the dietary supplement may further include vitamin E or a derivative thereof. In some embodiments, the dietary supplement may further include one or more secondary agent selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, guggulipds, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote general health.

Embodiments of the invention also include methods for preparing a nitro-fatty acid by isolating nitro fatty acids from fish oil. Other methods for preparing a nitro fatty acid include the steps of contacting an existing unsaturated fatty acid with a nitro containing compound; and reacting an existing unsaturated fatty acid with a nitro containing compound to form a nitro fatty acid. Still other methods for preparing activated fatty acids include the steps of contacting an unsaturated fatty acid with a mercuric salt and a selenium compound; contacting an intermediate resulting from step 1 with an electron withdrawing group donating reagent; reacting the intermediate resulting from step 2 with an oxidizing agent. Yet other methods for preparing nitro fatty acids include the steps of combining a first component at least comprising an aliphatic hydrocarbon having an electron withdrawing group at one end and a second component at least comprising aliphatic hydrocarbon chain having an aldehyde at one end in the presence of a base to form a first intermediate; generating an alkene from the first intermediate.

DESCRIPTION OF DRAWINGS

FIG. 1 is a graph showing stability of 10-nitro oleic acid in olive oil over a period of 19 days at 22° C., 37° C. and 50° C. Stability is plotted as a percentage of the starting concentration of 10-nitro oleic acid.

BACKGROUND

Nitric oxide (NO) is an endogenously generated, lipophilic signaling molecule that has been implicated in the maintenance of vascular homeostasis, modulation of oxygen radical reactions, inflammatory cell function, post-translational protein modification and regulation of gene expression. In addition, nitric oxide-derived species display separate and unique pharmacological properties, specifically can mediate oxidation and nitration of biomolecules such as, for example, unsaturated fatty acids.

Various reactions yield products capable of concerted oxidation, nitrosation and nitration of target molecules. For example, nitric oxide may react with superoxide ($O_2^-$) to yield peroxynitrite ($ONOO^-$) and its conjugate acid, peroxynitritrous acid ($ONOOH$), the latter of which may undergo homolytic scission to form nitrogen dioxide (.$NO_2$) and hydroxyl radical (.OH). In some instances, biological conditions may favor the reaction of $ONOO^-$ with $CO_2$ which yields nitrosoperoxycarbonate ($ONOOCO_2^-$), which rapidly yields .$NO_2$ and carbonate (.$CO_3^-$) radicals via homolysis or rearrangement to $NO_3^-$ and $CO_2$. During inflammation, neutrophil myeloperoxidase and heme proteins such as myoglobin and cytochrome c catalyze $H_2O_2$-dependent oxidation of nitrite ($NO_2^-$) to .$NO_2$, resulting in biomolecule oxidation and nitration that is influenced by the spatial distribution of catalytic heme proteins. The reaction of .NO with $O_2$ can also produce products that can be substrates or reactants for nitrosation and nitration. For example, the small molecular radius, uncharged nature and lipophilicity of .NO and $O_2$ facilitate concentration of these species in biological membranes in a process referred to as the "molecular lens" effect. The increase in concentration induced by .NO and $O_2$ solvation in hydrophobic cell compartments accelerates the normally slow reaction of .NO with $O_2$ to yield $N_2O_3$ and $N_2O_4$. Finally, environmental sources also yield .$NO_2$ as a product of photochemical air pollution and tobacco smoke.

Nitration of fatty acids by .$NO_2$ can occur through several methods. For example, during both basal cell signaling and tissue inflammatory conditions, .$NO_2$ can react with membrane and lipoprotein lipids. In both in vivo and in vitro systems, .$NO_2$ has been shown to initiate radical chain autoxidation of polyunsaturated fatty acids via hydrogen abstraction from the bis-allylic carbon to form nitrous acid and a resonance-stabilized bis-allylic radical. Depending on the radical environment, the lipid radical species can react with molecular oxygen to form a peroxyl radical, which can react further to form lipid hydroperoxides then oxidized lipids. During inflammation or ischemia, when $O_2$ levels are lower, lipid radicals can react to an even greater extent with .$NO_2$ to generate multiple nitration products including singly nitrated, nitrohydroxy- and dinitro-fatty acid adducts. These products can be generated via hydrogen abstraction, direct addition of .$NO_2$ across the double bond, or both, and in some cases, such reactions may be followed by further reactions of the intermediate products that are formed. Hydrogen abstraction causes a rearrangement of the double bonds to form a conjugated diene; however, the addition of .$NO_2$ maintains a methylene-interrupted diene configuration to yield singly nitrated polyunsaturated fatty acids. This arrangement is similar to nitration products generated by the nitronium ion ($NO_2^+$), which can be produced by $ONOO^-$ reaction with heme proteins or via secondary products of $CO_2$ reaction with $ONOO^-$.

The reaction of polyunsaturated fatty acids with acidified nitrite ($HNO_2$) can generate a complex mixture of products similar to those formed by direct reaction with .$NO_2$, including the formation of singly nitrated products that maintain the bis-allylic bond arrangement. The acidification of $NO_2^-$ can create a labile species, $HNO_2$, which is in equilibrium with secondary products, including $N_2O_3$, .NO and .$NO_2$, all of which can participate in nitration reactions. The relevance of this pathway as a mechanism of fatty acid nitration is exemplified by physiological and pathological conditions wherein $NO_2^-$ is exposed to low pH (e.g., <pH 4.0). This may conceivably occur in the gastric compartment, following endosomal or phagolysosomal acidification or in tissues following-post ischemic reperfusion.

Nitrated linoleic acid ($LNO_2$) has been shown to display robust cell signaling activities that are generally anti-inflammatory in nature. Synthetic $LNO_2$ can inhibit human platelet function via cAMP-dependent mechanisms and inhibits neutrophil $O_2^-$ generation, calcium influx, elastase release, CD11b expression and degranulation via non-cAMP, non-cGMP-dependent mechanisms. $LNO_2$ may also induce vessel relaxation in part via cGMP-dependent mechanisms. In aggregate, these data, derived from a synthetic fatty acid infer that nitro derivatives of fatty acids ($NO_2$—FA) represent a novel class of lipid-derived signaling mediators. To date, a gap in the clinical detection and structural characterization of nitrated fatty acids has limited defining $NO_2$—FA derivatives as biologically-relevant lipid signaling mediators that converge .NO and oxygenated lipid signaling pathways.

The metabolism of arachidonic acid is a key element of inflammation. In acute inflammation, there is typically a respiratory burst of neutrophil activity that initiates cascades involving a change in the oxidation state of the cell. Alteration in the redox state of the cell activates transcription factors such as NFκB as well as AP1, which then causes production of proinflammatory mediators. These mediators, such as Tumor necrosis factorA (TFα) and various interleukins, cause a burst of other cytokines. Arachadonic acid is released, which is oxidized to biologically active mediators. When arachadonic acid is oxidized via the cyclooxygenase or lipoxygenase pathways, eicosanoids e.g. prostaglandins, leukotrines, and hyroxyeicosatetraenoic acid (HETE) are produced, which cause erythma, edema, and free radical production.

Acute inflammation is often characterized by the generation of excited oxygen species, e.g. superoxide anion, which damages the lipid-rich membranes and activate the chemical mediators of the proinflammation and inflammation cascades. These oxygenated species tend to concentrate in hydrophobic regions. Both in or near these hydrophobic compartments, .NO and NOx undergo a rich spectrum of reactions with oxygen species, transition metals, thiols, lipids, and a variety of organic radicals. These multifaceted reactions yield reactive species that transduce .NO signaling and modulate tissue inflammatory responses.

During inflammation, adaptive and protective responses are elicited by vascular and other tissues to protect the host from its own mechanisms directed at destroying invading pathogens. Heme oxygenase 1 (HO-1) plays a central role in vascular inflammatory signaling and mediates a protective response to inflammatory stresses such as atherosclerosis, acute renal failure, vascular restenosis, transplant rejection, and sepsis. Heme oxygenase 1 catalyzes the degradation of heme to billverdin, iron, and CO, the last of which has been shown to display diverse, adaptive biological properties, including anti-inflammatory, anti-apoptotic, and vasodilatory actions. During inflammation, HO-1 gene expression is up-regulated, with induction typically occurring transcriptionally. Neutrophil myeloperoxidase and heme proteins such as myoglobin and cytochrome c catalyze $H_2O_2$-dependent oxidation of nitrite ($NO_2$) to $NO_2$, resulting in biomolecule oxidation and nitration that is influenced by the spatial distribution of catalytic heme proteins. These and other products are capable of concerted oxidation, nitrosation and nitration of target molecules.

The body contains an endogenous antioxidant defense system made up of antioxidants such as vitamins C and E, glutathione, and enzymes, e.g., superoxide dismutase. When metabolism increases or the body is subjected to other stress such as infection, extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage or proteins and lipoproteins, and oxidation of membrane lipids and lipoproteins.

Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

It would be desirable to have topical treatments for rosacea, eczema, acne, alopecia, psoriasis and inflammatory conditions in general using compositions which disrupt the inflammatory cascades describes above.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient, whereby the therapeutic positively impacts the tissue to which it is targeted. Thus, as used herein, the term "administering", when used in conjunction with a nitrated lipid can include, but is not limited to, providing a nitrated lipid to a subject systemically by, for example, intravenous injection, whereby the therapeutic reaches the target tissue. "Administering" a composition may be accomplished by, for example, injection, oral administration, topical administration, or by these methods in combination with other known techniques. Such combination techniques include heating, radiation, ultrasound and the use of delivery agents.

The term "animal" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

"Nutraceutical" as used herein generally refer to natural, bioactive chemical compounds that provide physiological benefits, including, disease prevention and health promotion which may be used to supplement the diet. Nutraceuticals can be either purified or concentrated by using bioengineering methods and can be enhanced through genetic methods, which contain elevated levels of natural substances. Examples of nutraceuticals include isolated nutrients and herbal products and generally contain at least one of the following ingredients: a vitamin, a mineral, an herb or other botanical, an amino acid, a metabolite, constituent, extract, or combination of these ingredients. Common examples of nutraceuticals include beta-carotene, ephedra, ginko biloba, goldenseal, valerian, ginseng, and echinacea. The nutraceuticals described herein may be useful for maintenance and support of, for example, healthy joints, skin, and eye and brain function.

As used herein, the term "therapeutic" means an agent utilized to treat, combat, ameliorate, prevent or improve an unwanted condition or disease of a patient. In part, embodiments of the present invention are directed to the treatment of inflammation, obesity-related diseases, metabolic diseases, cardiovascular diseases, cerebrovascular and neurodegenerative diseases, cancer or the aberrant proliferation of cells.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

As used herein and in the attached claims, the term "enriched" shall mean that the composition or portion of the composition includes a concentration of the identified component that is greater than the amount of the component naturally occurring in the composition. For example, with reference to activated fatty acids a composition enriched for activated fatty acids may include greater than at least 50 nM activated fatty acids. Therefore, a composition that is enriched for activated fatty acids may be at least 0.05% by weight activated fatty acid, at least 0.1% by weight activated fatty acid, at least 0.15% by weight activated fatty acid, at least 0.25% by weight activated fatty acid, at least 0.5% by weight activated fatty acid, at least 1.0% by weight activated fatty acid, at least 2% by weight activated fatty acid, and so on.

Generally speaking, the term "tissue" refers to any aggregation of similarly specialized cells which are united in the performance of a particular function.

Embodiments of the invention presented herein are generally directed to activated fatty acids and, in particular, activated unsaturated fatty acids. As used herein an "activated fatty acid" refers to a fatty acid having at least one electron withdrawing group covalently bound to a carbon of the saturated or unsaturated aliphatic chain of a fatty acid. Such activated fatty acids may be substituted by any number of electron withdrawing groups at any number of positions on the hydrocarbon chain, and an electron withdrawing group may be positioned in either cis or trans configuration at a double bond or in either R or S absolute stereochemistry at an $sp^3$ chiral/stereogenic center. For example, in one embodiment, an activated fatty acid may have one electron withdrawing group, and in another, an activated fatty acid may be substituted with multiple electron withdrawing groups at multiple positions along the hydrocarbon chain. While the activated fatty acids of the invention may have an electron withdrawing group positioned at any carbon along the aliphatic hydrocarbon chain between the carboxy terminal carbon to the terminal methyl ($\omega$), in some embodiments, the electron withdrawing group may be positioned within about 1 carbon from the carboxy terminal carbon and within about 1 carbon from the terminal methyl. In other embodiments, the electron withdrawing group may be positioned within about 3 carbons of either the carboxy terminal carbon and/or the methyl terminal carbon, and in still others embodiments, the electron withdrawing group may be positioned within 5 carbons of either of the carboxy terminal carbon and/or the methyl terminal carbon.

In certain embodiments, the electron withdrawing group may be positioned on a carbon directly attached to a double bond of the activated fatty acid forming an "electron withdrawing vinyl" group. The electron withdrawing group of such vinyl groups may be on either side of the double bond. Fatty acids encompassed by embodiments of the invention may have one or more than one electron withdrawing vinyl groups at any carbon on the aliphatic hydrocarbon chain, and there are several ways that an unsaturated fatty acid can have one electron-withdrawing group. In one embodiment, an activated oleic acid (ocatadecac-9-enoic acid) which is an 18 carbon, $\omega$-6 fatty acid with one double bond (denoted "18:1") between the $6^{th}$ (C-13) and $7^{th}$ (C-12) carbons, may have an electron withdrawing group at either C-13 or C-12. In another exemplary embodiment, an activated linoleic acid (octadeac-9,12-dienoic acid), which is an 18 carbon, $\omega$-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at C-9 or C-10 or C-12 or C-13. Similarly, other polyunsaturated fatty acids, with 3, 4, 5, 6 or more double bonds, can have one electron withdrawing at either position on any of the double bond carbons, including all possible permutations of positions and electron-withdrawing groups.

In other embodiments, a mono or polyunsaturated fatty acid may have two electron-withdrawing groups, and there are several ways that an unsaturated fatty acid can have two electron-withdrawing groups. For example, in one embodiment, an activated oleic acid (ocatadecac-9-enoic acid) which is an 18 carbon, $\omega$-6 fatty acid with one double bond (denoted "18:1") between the $6^{th}$ (C-13) and $7^{th}$ (C-12) carbons, may have an electron withdrawing group at both C-13 and C-12. In another exemplary embodiment, an activated linoleic acid (octadeac-9,12-dienoic acid), which is an 18 carbon, $\omega$-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at any two of the positions C-9, C-10, C-12 or C-13, with the following possible permutations: C-9 and C-10, C-9 and C-12, C-9 and C-13, C-10 and C-12, C-10 and C-13, or C-12 and C-13. Similarly, other polyunsaturated fatty acids, with 3, 4, 5, 6 or more double bonds, can have two electron withdrawing at two of the positions on any of the double bond carbons, including all possible permutations of positions and electron-withdrawing groups.

In analogy to the preceding descriptions of compounds with one electron-withdrawing group or two electron-withdrawing groups, it is also possible to have three, four, five or more electron withdrawing groups. Following the same logic above, in the preceding descriptions of compounds with one electron-withdrawing group or two electron-withdrawing groups, polyunsaturated fatty acids, with 3, 4, 5, 6 or more double bonds, can have multiple electron withdrawing (three, four, five or more, as available positions for substitution permit) at any of the positions on any of the double bond carbons, including all possible permutations of positions and electron-withdrawing groups.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ ($\sigma$ [P]) is about −0.7 and the $\sigma$ [P] for a nitro group is about 0.8.

Embodiments of the invention encompass any known electron withdrawing group. For example, electron-withdrawing groups may include, but are not limited to, aldehyde (—COH) acyl (—COR), carbonyl (—CO), carboxylic acid (—COOH), ester (—COOR), halides (—Cl, —F, —Br, etc.), fluoromethyl (—$CF_n$), cyano (—CN), sulfonyl (—$SO_n$), sulfone (—$SO_2R$), sulfonic acid (—$SO_3H$), 1°, 2° and 3° ammonium (—$NR_3^+$), and nitro(—$NO_2$). In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl. In other embodiments, the activated fatty acids of the invention may be additionally substituted by non-electron withdrawing groups or electron donating groups including, for example, alcohol (—OH), reverse ester (—OOCR), alkyl, alkenyl, alkynyl, 1° and 2° amines (—NR$_2$), nitrate (—ONO$_2$), nitrito (—ONO) and the like.

The fatty acids of various embodiments may be any unsaturated and polyunsaturated fatty acid known in the art. The term "fatty acid" describes aliphatic monocarboxylic acids. Various embodiments include nitrated fatty acid having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons. Embodiments of the invention encompass such naturally occurring fatty acids as well as non-naturally occurring fatty acids which may contain an odd number of carbons and/or a non-naturally, occurring linker. Some embodiments of the invention include fatty acids having from 8 to 23 carbons, and others include fatty acids having from 12 to 18 carbons in the aliphatic hydrocarbon chain. In still other embodiments, fatty acids may have greater than 24 carbons in the aliphatic hydrocarbon chain. The fatty acids of the invention may also be branched at one or more location along the hydrocarbon chain, and in various embodiments, each branch may include an aliphatic hydrocarbon chain of from 1 to 24 carbons, 2 to 20 carbons or 4 to 18 carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is actually an E nitroalkene. Similarly, the nitroalkene analog of a "trans" double bond is actually a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega (ω-3, ω-5, ω-6, ω-7, ω-9 fatty acids and the like. Any such fatty acid may be useful in embodiments of the invention. The symbol 'ω' is used to refer to the terminal methyl carbon of the aliphatic hydrocarbon chain. The placement of the double bond of the ω-X fatty acid is the carbon-carbon bond X number of carbons from the w carbon. For example, an ω-6 fatty acid has a double bond between the 6th and 7$^{th}$ carbons counting backward from the ω carbon and an ω-3 fatty acid has a double bond between the 3$^{rd}$ and 4$^{th}$ carbons counting backward from the ω carbon. Various embodiments of the invention include nitrated ω-3 fatty acids, including, but not limited to, linolenic acid, alpha-linolenic acid, eicosapentanoic acid, docosapentaenoic acid, docosahexanoic acid and stearidonic acid; nitrated ω-5 fatty acids including, but not limited to, myristoleic acid; nitrated ω-6 fatty acids including, but not limited to, linoleic acid, gamma-linoleic acid, dihomo-gamma-linoleic acid and arachidonic acid; nitrated ω-7 fatty acids including, but not limited to, palmitoleic acid; and nitrated ω-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid. Embodiments of the invention also include synthetic equivalents to naturally occurring fatty acids and derivatives thereof.

In particular embodiments, the fatty acids utilized in embodiments of the invention may be omega-3 fatty acids. As used herein, the term "omega-3 fatty acids" or "ω-3 fatty acids" may include natural or synthetic omega-3 fatty acids, or pharmaceutically acceptable esters, derivatives, conjugates (see, e.g., U.S. Publication No. 2004/0254357 to Zaloga et al. and U.S. Pat. No. 6,245,811 to Horrobin et al., each of which is hereby incorporated by reference in its entirety), precursors or salts thereof and mixtures thereof. Examples of ω-3 fatty acid oils include but are not limited to ω-3 polyunsaturated, long-chain fatty acids such as a eicosapentaenoic acid (EPA), docosahexaenoic acid (DHA), and α-linolenic acid; esters of ω-3 fatty acids with glycerol such as mono-, di- and triglycerides; and esters of the ω-3 fatty acids and a primary, secondary or tertiary alcohol such as fatty acid methyl esters and fatty acid ethyl esters. In certain embodiments, the ω-3 fatty acid oils may be long-chain fatty acids such as EPA or DHA, triglycerides thereof, ethyl esters thereof and mixtures thereof. The ω-3 fatty acids or their esters, derivatives, conjugates, precursors, salts and mixtures thereof can be used either in their pure form or as a component of an oil, such as fish oil, preferably purified fish oil concentrates.

Various fish oils are known and useful as sources for ω-3, ω-6, and ω-9 fatty acids, and any such oil may be used in embodiments of the invention. For example, oils derived from herring, sardines, mackerel, lake trout, flounder, albacore tuna, krill, and salmon are useful sources of ω-3, ω-6, and ω-9 fatty acids.

Commercially available ω-3 fatty acids suitable for use in the invention may include, but are not limited to, Incromega F2250, F2628, E2251, F2573, TG2162, TG2779, TG2928, TG3525 and E5015 (Croda International PLC, Yorkshire, England), and EPAX6000FA, EPAX5000TG, EPAX4510TG, EPAX2050TG, K85TG, K85EE, K80EE and EPAX7010EE (Pronova Biocare a.s., 1327 Lysaker, Norway). In certain embodiments, the ω-3 fatty acids may be a mixture of several ω-3 fatty acids such as OMACOR™ omega-3 fatty acids which are combinations of EPA and DHA ω-3 fatty acids, and are described in U.S. Pat. Nos. 5,502,077, 5,656,667 and 5,698,594, which are hereby incorporated by reference in their entireties.

Similarly various plant oils are known and useful as sources for ω-3, ω-6, and ω-9 fatty acids, and any such oil may be used in embodiments of the invention. For example, olive oil, peanut oil, grape seed oil, sea buckthorn oil, sesame oil, and f poppyseed oil are useful sources of ω-3, ω-6, and ω-9 fatty acids, and in particular ω-9 fatty acids, such as, oleic acid. http://en.wikipedia.org/wiki/Oleic_acid-cite_note-pmid17093176-2#cite_note-pmid17093176-2

Other embodiments of the invention include unsaturated or polyunsaturated non-naturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups which interrupt the aliphatic hydrocarbon chain. For example, in some embodiments, activated fatty acids may have one or more non-carbon-carbon linkage such as, for example, ester, ether, vinyl ether, amino, imine and the like at any position within the aliphatic hydrocarbon chain.

For example, embodiments of the invention include compounds of general formulae I and II:

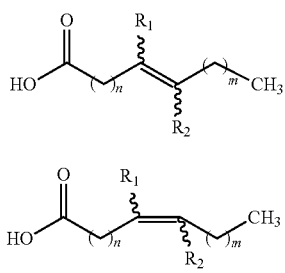

wherein $R_1$ and $R_2$ are independently selected from —H and any electron withdrawing groups including, but not limited to —COH, —COR, —CO, —COOH, —COOR, —Cl, —F, —Br, —I, —CF$_3$, —CN, —SO$_3^-$, —SO$_2$R, —SO$_3$H, —NH$_3^+$, —NHR$_2^+$, —NHR$_2$R$^+$, —NR$_3^+$ and —NO$_2^-$ wherein at least one of $R_1$ and $R_2$ is an electron withdrawing group and m and n are, independently, 1-20. Some embodiments include compounds of general formula III:

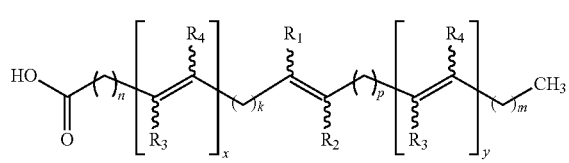

wherein $R_1$, $R_2$, m and n are as described above, $R_3$ and $R_4$ are, independently, selected from —H, —COH, —COR, —CO, —COOH, —COOR, —Cl, —F, —Br, —I, —CF$_3$, —CN, —SO$_3^-$, —SO$_2$R, —SO$_3$H, —NH$_3^+$, —NH$_2$R$^+$, —NHR$_2^+$, —NR$_3^+$ and —NO$_2^-$; k and p are, independently, 0 to 5 and x and y are independently, 0 to 3, and wherein each double bond is in either cis or trans configuration. In still other embodiments, any carbon associated with m, n, k or p may be substituted.

The activated fatty acids described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloropropane, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of activated fatty acids of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, beta.-hydroxybutyric, galactaric and galacturonic acids.

Suitable pharmaceutically acceptable base addition salts used in connection with the activated fatty acids of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Activated fatty acids as described in various embodiments of the invention above, may be administered to individuals to treat, ameliorate and/or prevent a number both acute and chronic inflammatory and metabolic conditions. In particular embodiments, activated fatty acids may be used to treat acute conditions including general inflammation, arterial stenosis, organ transplant rejection and burns, and chronic conditions such as, chronic lung injury and respiratory distress, diabetes, hypertension, obesity, rheumatoid arthritis, neurodegenerative disorders and various skin disorders. However, in other embodiments, activated fatty acids may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

For example, in one embodiment, an activated fatty acid may be administered to treat hypertension by lowering blood pressure to normal levels without reducing the blood pressure of the individual below normal levels even if the activated fatty acid is over-administered. Thus, without wishing to be bound by theory, the activated fatty acids of the invention may provide treatment of an individual without the negative affects associated with over-administration or over-treatment using traditional medications.

In a still further embodiment, activated fatty acids may be useful for ischemic preconditioning or protecting the heart from ischemic injury due to vessel spasm or blockage. For example, nitrated fatty acids produced by mitochondria in cells under ischemic conditions cause a number of physiological changes within the cell that increases cell survival under ischemic conditions. By providing activated fatty acids to an individual, similar ischemic preconditioning or protection may be achieved allowing for improved survival of, for example, cardiac tissue under ischemic conditions or organs being preserved for optimizing viability and function upon transplantation. In particular embodiments, nutraceuticals including activated fatty acids may be provided to individuals at risk of heart disease, heart attack, heart failure, vascular blockage, arrhythmia, atrial fibrillation, heart valve diseases, cardiomyopathy, and the like to both reduce or alleviate the symptoms of such maladies and to increase the likelihood of survival in the event of, for example, a heart attack, arrhythmia, or arterial fibrillation or to more generally improve heart or circulatory system function.

In addition, activated fatty acid administration may be useful for activating a number of other factors important for cell signaling. For example, in one embodiment, activated fatty acids may be administered to induce gene expression and tissue activity of heme oxygenase-1 (HO-1) which has been shown to mediate adaptive and protective responses during inflammation, and activation of an adaptive or protective inflammatory response mediated by HO may be useful in treating inflammatory diseases such as, but not limited to, atherosclerosis, acute renal failure, vascular restinosis, transplant rejection, and sepsis. Thus, activated fatty acids may be useful for treating general inflammation resulting from surgery, injury or infection.

The nutraceuticals of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, ocular, intravaginally, or inhalation. In certain embodiments, the administration may be parenteral. In some embodiments, the nutraceutical may be prepared in the presence or absence of stabilizing additives that favors extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an activated fatty acid may be deposited to a site of injury or inflammation, such as, for example, the site of a surgical incision or a site of inflammation due to arthroscopy, angioplasty, stent placement, by-pass surgery and so on.

When administered, activated fatty acids may interact with a number of cellular receptors and/or proteins that mediate inflammation, either by inhibiting or stimulating their activity thereby inhibiting or reducing inflammation. Without wishing to be bound by theory, activated fatty acids may modulate important signaling activities including, for example, neurotransmission, gene expression, vascular function and inflammatory responses, and chemical properties of activated fatty acids that may facilitate these activities include, but are not limited to, the strong, reversible electrophilic nature of the β carbon adjacent to the electron withdrawing vinyl group, an ability to undergo Nef-like acid base reactions to release NO, an ability to partition into both hydrophobic and hydrophilic compartments, and a strong affinity for G-protein coupled receptors and nuclear receptors.

For example, in one embodiment, activated fatty acids may be administered to mediate cell signaling via multiple G-protein coupled receptors and nuclear receptors such as, but not limited to, peroxisome proliferator-activated receptors (PPAR) including PPARα, PPARγ, and PPARδ. PPAR is a nuclear receptor that is expressed throughout an organism, including in monocytes/macrophages, neutrophils, endothelial cells, adipocytes, epithelial cells, hepatocytes, mesangial cells, vascular smooth muscle cells, neuronal cells and when "activated" induces transcription of a number of target genes. Activation of PPAR has been shown to play various roles in regulating tissue homeostasis including, for example, increasing insulin sensitivity, suppress chronic inflammatory processes, reduce circulating free fatty acid levels, correct endothelial dysfunction, reduce fatty streak formation, delay plaque formation, limit blood vessel wall thickening and enhance plaque stabilization and regression. The activated fatty acids embodied herein may perform each of these functions associated with PPAR activation.

Moreover, activated fatty acids may perform these functions without significantly altering normal cellular process. For example, in one embodiment, an activated fatty acid may be administered to treat hypertension by lowering blood pressure to normal levels without reducing the blood pressure of the individual below normal levels even if the activated fatty acid is over-administered. Thus, without wishing to be bound by theory, the activated fatty acids of the invention may provide treatment of an individual without the negative affects associated with over-administration or over-treatment using traditional medications.

Activation of PPAR has been shown to be induced by a locking reaction in which a critical thiol in a highly conserved cysteine (Cys 285 of human PPARγ) which is located in a ligand binding domain of PPAR. Partial activation of PPAR has been shown to occur when relatively high concentrations of known thiol reactive compounds, such as 15-deoxy-$\Delta^{12,14}$-prostaglandin $J_2$ (15-d $PGJ_2$), are administered. Without wishing to be bound by theory, activated fatty acids may bind to PPAR covalently at the reactive thiol in the ligand binding domain of PPAR. Moreover, activated fatty acids may induce a conformational change in PPAR. More specifically, activated fatty acid binding may result in the C-terminus of the ligand binding domain (α-helix 12) to adopt an active conformation that may promote a beneficial pattern of co-repressor release and co-activator recruitment. Thus, activated fatty acids may enhance PPAR activation and transcription of PPAR regulated genes beyond that of known PPAR activating compounds.

In addition to activation of PPAR, activated fatty acid administration may be useful for activating a number of other factors important for cell signaling. For example, in one embodiment, activated fatty acids may be administered to induce gene expression and tissue activity of heme oxygenase-1 (HO-1) which has been shown to mediate adaptive and protective responses during inflammation, and activation of an adaptive or protective inflammatory response mediated by HO may be useful in treating inflammatory diseases such as, but not limited to, atherosclerosis, acute renal failure, vascular restinosis, transplant rejection, and sepsis. In another embodiment, activated fatty acids may induce a reversible post-translational modification of proteins, such as, for example, glutathione (GSH) and glyceraldehyde-3-phosphate dehydrogenase (GAPDH) by covalently binding to catalytic cysteines on such proteins. Without wishing to be bound by theory, the covalent modification of these proteins by activated fatty acids may increase the hydrophobicity of these proteins inducing translocation of to membranes and suggests a role for redox regulation of enzyme function, cell signaling and protein trafficking. In yet another embodiment, activated fatty acids may be administered to repress NF-κB dependent gene expression and endothelial tumor necrosis factor-α induced expression of vascular cell adhesion molecules in monocytes and macrophages which results in inhibition of rolling and adhesion during inflammation. Thus, activated fatty acids may be useful for treating general inflammation resulting from surgery, injury or infection. In a further embodiment, activated fatty acids may be administered to limit tissue inflammatory injury and inhibit the proliferation of vascular smooth muscle cells by increasing cellular levels of nuclear factor erythroid 2-related factor-2 (Nrf-2) which may be useful in the treatment of a number of vascular diseases. In a still further embodiment, activated fatty acids may be useful for ischemic preconditioning. For example, nitrated fatty acids produced by mitochondria in cells under ischemic conditions cause a number of physiological changes within the cell that increases cell survival under ischemic conditions. By providing activated fatty acids to an individual, similar ischemic preconditioning may be achieved allowing for improved survival of, for example, cardiac tissue under ischemic conditions or organs being preserved for optimizing viability and function upon transplantation.

The activated fatty acids of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including an activated fatty acid may be deposited to a site of injury or inflammation, such as, for example, the site of a surgical incision or a site of inflammation due to arthroscopy, angioplasty, stent placement, by-pass surgery and so on.

In certain other embodiments, the compounds of the invention may be applied locally as a salve or lotion applied directly to an area of inflammation. For example, in some embodiments, a lotion or salve including activated fatty acids of the invention may be prepared and applied to a burn, radiation burn, site of dermal disorder, edema, arthritic joint or the like. Such salves and lotions, may include a topical formulation of one or more activated fatty acid in a dermatologically acceptable vehicle, and in particular embodiments, the topical formulation may as a nutraceutical salve or lotion which may contain for example, hyaluronic acid, chondroitin sulphate, collagen glucosamine, keratan sulphate, dermatan sulphate, vitamin C, green tea extract, shea butter, grape-seed extract, aloe extract, or mixtures thereof.

Various embodiments, of the invention are also directed to method for administering activated fatty acids. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

In various embodiments, an effective amount of an activated fatty acid delivered during each administration cycle may range from about 10 $mg/m^2$/day to about 1000 $mg/m^2$/day. In some embodiments, an effective amount may be about 20 $mg/m^2$/day to about 700 $mg/m^2$/day, and in others, an effective amount may be about 30 $mg/m^2$/day to about 600 $mg/m^2$/day. In particular embodiments, an effective amount may be about 50 $mg/m^2$/day, about 400 $mg/m^2$/day, about 500 $mg/m^2$/day, or about 600 $mg/m^2$/day. In yet other embodiments, an effective amount of an activated fatty acid may vary as treatment progresses. For example, a dosage regimen may be increased or decreased as treatment proceeds through administration cycles, or the daily dosage may increase or decrease throughout administration. In additional embodiments, greater than 1000 $mg/m^2$/day may be administered because even high doses of activated fatty acid are generally tolerable to the patient and may not produce undesired physiological effects.

In some embodiments, activated fatty acids administered may include up to at least 40% by weight, at least 50% by weight, at least 60% by weight at least 70% by weight, at least 80% by weight, at least 90% by weight or at least 100% by weight of one or more species of activated fatty acid. In particular embodiments, a single species of activated ω-3 fatty acid may make up at least 50%, at least 60% by weight, at least 70% by weight, at least 80% of the total activated fatty acid administered, and in other embodiments, a single species of activated omega-3 fatty acids may make up about 5 to about 100% by weight, about 25 to about 75% by weight, or about 40 to about 55% by weight of the fatty acids administered. In particular embodiments, the ratio of activated fatty acid to non-activated may be from about 99:1 to about 1:99, about 99:1 to about 90:10, about 90:10 to about 80:20, about 80:20 to about 70:30, about 70:30 to about 60:40, about 60:40 to about 50:50, about 50:50 to about 40:60, about 40:60 to about 30:70, about 30:70 to about 20:80, about 20:80 to about 10:90, about 10:90 to about 1:99 about 1:4 to about 4:1, about 1:3 to about 3:1 or about 1:2 to about 2:1.

In yet other embodiments activated fatty acids administered may include up to at least 0.01%, 0.025%, 0.05%, 0.1%, 0.5%, 1.0%, 10.0%, 20.0% and 30.0% by weight of one or more species of activated fatty acid.

For example, in some embodiments, the activated omega-3 fatty acids may be prepared from one of EPA or DHA or a combination of EPA and DHA. The composition administered may include about 5 to about 100% by weight, about 25 to about 75% by weight, or about 30 to about 60% by weight activated EPA and/or activated DHA, and any remainder may be made up of non-activated EPA and/or DHA. In compositions containing both activated EPA and activated DHA, the activated EPA and activated DHA may be present in a weight ratio of EPA:DHA of from 99:1 to 1:99, 1:4 to 4:1, 1:3 to 3:1 or 1:2 to 2:1. In compositions containing activated EPA and/or activated DHA as well as non-activated EPA and/or DHA, the weight ratio of activated:non-activated may be from 99:1 to 1:99, 99:1 to 90:10, 90:10 to 80:20, 80:20 to 70:30, 70:30 to 60:40, 60:40 to 50:50, 50:50 to 40:60, 40:60 to 30:70, 30:70 to 20:80, 20:80 to 10:90, 10:90 to 1:99, 1:4 to 4:1, 1:3 to 3:1 or 1:2 to 2:1. In the embodiments described above, the percentage by weight may be based on the free acid or ester forms, although it is preferably based on the ethyl ester form of the ω-3 fatty acids even if other forms are utilized in accordance with the present invention.

In still other embodiments, the activated fatty acid may be prepared from a different base fatty acid than the non-activated fatty acids with which it is combined. For example, in some embodiments, the activated fatty acid may be an activated linoleic acid, an activated oleic acid, or combinations thereof, and these activated fatty acids may be combined with non-activated EPA and/or DHA. In such embodiments, the ratio of activated linoleic acid and/or activated oleic acid to non-activated EPA and/or DHA may be from about 99:1 to 1:99, 99:1 to 90:10, 90:10 to 80:20, 80:20 to 70:30, 70:30 to 60:40, 60:40 to 50:50, 50:50 to 40:60, 40:60 to 30:70, 30:70 to 20:80, 20:80 to 10:90, 10:90 to 1:99, 1:4 to 4:1, 1:3 to 3:1, 1:2 to 2:1, or 1:1. In particular embodiments, activated linoleic acid or oleic acid may be combined with EPA and DHA, and each of the three components may be provided in a ratio of from about 1:1:1, 2:1:1, 1:2:1, 1:1:2, 2:2:1, 1:2:2, 3:1:1, and the like.

In some embodiments, the dosage regimen as described above may be combined with a secondary form of treatment or a secondary agent. For example, activated fatty acids such as those described above may be combined with antioxidants, statins, squalene synthesis inhibitors, azetidinone-based compounds, LDL catabolism activators, PPAR antagonists or agonists, antiarrhythmic agent, NSAIDs and the like, and combinations thereof.

In particular embodiments, the activated fatty acids of the invention may be mixed with one or more nutraceutical equivalents to any of the agents described above. For example, in some embodiments, the activated fatty acids of the invention may be mixed with a nutraceutical statin equivalent such as, for example, from rice bran oil, enzyme-treated stabilized rice bran, a solubilized fraction of rice bran oil, and derivatives thereof and the like. In other embodiments, one or more nutraceutical including, but not limited to, glucosamine derivatives, methylsulfonylmethane, yucca concentrates, grape seed extracts, beta-carotene, ephedra, ginko biloba, goldenseal, valerian, ginseng, echinacea, and the like may be combined with activated fatty acids.

Embodiments further include nutraceuticals including the nutraceutical equivalents to any of the agents described above and one or more activated fatty acids. Thus, in certain embodiments, the nutraceuticals may include one or more activated fatty acid in combination with one or more other nutraceutical compound or one or more other secondary agent. Nutraceuticals containing various combinations of ingredients are well known in the art, and any known nutraceutical may be combined with one or more activated fatty acids to produce a combination nutraceutical. For example, in various embodiments, activated fatty acids may be combined with vitamins including vitamins A, B, including vitamin B-1, B-2, B-6, B-12, C, D including vitamin D3, and E, and the like and derivatives thereof, minerals such as selenium and the like, plant extracts such as β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, and the like, nutraceutical oils such as flaxseed oil, borage seed oil, and other know nutraceutical components such as coenzyme Q10, glucosamine derivatives, methylsulfonylmethane, pantothenic acid, biotin, thiamin, riboflavin, niacin, folic acid, palmitic acid, and the like. Thus, without wishing to be bound by theory, nearly any nutraceutical can be incorporated into the activated fatty acid containing nutraceuticals described herein.

In particular embodiments, one or more additional ingredients may be provided to produce a nutraceutical for treating or preventing specific diseases or indication. For example, in some embodiments, activated fatty acids may be combined with other nutraceutically active components that can act as antioxidants such as vitamin C, vitamin E, vitamin D, selenium and the like to create a nutraceutical for treating aging and cancer. In other embodiments, a nutraceutical for treating or preventing diseases of the eye may be prepared by combining activated fatty acids with, for example, vitamin A and/or β-carotene, and in still other embodiments, a nutraceutical with neuroprotective activities or that enhances cognitive abilities may be prepared by combining activated fatty acids with, for example, ginko biloba. In yet other embodiments, nutraceuticals for treating or preventing heart or circulatory diseases may be prepared by combining activated fatty acids with policosanol, guggulipids, rice bran extract, enzyme-treated stabilized rice bran, a solubilized fraction of rice bran oil, wheat germ, wheat germ extract, beeswax, red yeast rice extract, and or other nutraceuticals known to exhibit statin-like activity. In further embodiments, components with various activities may be combined. For example, a nutraceutical with neuroprotective activities may include one or more antioxidants such as vitamin C, vitamin E, or selenium along with ginko biloba, since it is well known that antioxidants are also effective neuroprotectants. In yet other embodiments, vitamin E may be provided to any nutraceutical described herein to stabilize the activated fatty acids and increase the shelf life of the nutraceutical.

Nutraceuticals having fatty acids and one or more additional nutraceutically active components may be combined in a single dose formulation by known methods. For example, in some embodiments, lipophilic additional nutraceutically active components may be combined with the activated fatty acids directly. In other embodiments, the activated fatty acid may be separated from a non-lipophilic additional nutraceutically active component by, for example, preparing separate cores that are combined into a single capsule or incorporating the non-lipophilic additional nutraceutically active component into one or more coating layers.

In embodiments in which activated fatty acid are combined with a secondary form of treatment, the activated fatty acid may be administered in a separate dosage unit from the secondary agent such that each treatment is provided separately. In other embodiments, the activated fatty acid may be provided in the same dosage unit as one or more secondary agent. In such embodiments, the activated fatty acid may be combined with the one or more secondary agent in a range of about 1:1000 to about 1000:1 by weight or about 200:1 to about 200:1 by weight. For example, in some embodiments, the activated fatty acid may be present in an amount from about 1 mg to about 3000 mg or from about 10 mg to about 2000 mg, and the one or more secondary agents may be present in an amount from about 1 mg to about 1000 mg, about 5 mg to about 500 mg, and about 5 mg to about 100 mg.

In certain embodiments, a single dosage unit may include about 500 mg to about 2000 mg or about 1000 mg of one or more activated ω-3 fatty acids, and about 1 mg to about 150 mg or about 5 mg to about 100 mg of a statin compound, about 1 mg to about 300 mg or 10 to about 100 mg of a fibrate compound or a combination thereof.

The activated fatty acids of various embodiments may be prepared by any method known in the art. For example, in particular embodiments, the activated fatty acids may be derived from natural sources such as, for example, fish oils which may contain activated fatty acids, and in particular, nitro-fatty acids, that can be isolated, purified or concentrated form the fish oil. In other embodiments, an activated fatty acid may be prepared by contacting an naturally occurring unsaturated fatty acids with one or more nitro containing compounds or nitrogenating agents. Such naturally occurring activated fatty acids may be useful in the production of nutraceuticals.

In other embodiments, the method may be carried out in the presence of one or more cofactors and/or catalysts. For example, in certain embodiments, activated fatty acids may be prepared by combining an unsaturated fatty acid with a nitrogenating agent such as ammonia or primary amines, molecular oxygen and an oxidation catalyst as described in U.S. Pat. No. 4,599,430, which is hereby incorporated by reference in its entirety.

Methods for preparing activated fatty acids are incorporated by reference from U.S. applications 61/141,844 and US2010/01669218 A1.

Embodiments of the invention also include topical compositions containing activated fatty acids and, in some embodiments, one or more secondary agents and/or non-activated fatty acids. For example, in some embodiments, the topical composition may include one or more activated fatty acid. In such embodiments, the one or more activated fatty acids may comprise about 10% by weight to about 95% by weight of the total composition. In other embodiments activated fatty acids comprise about 0.01% to about 10% by weight of one or more species of activated fatty acid. In yet other embodiments activated fatty acids comprise about 95% to about 100% by weight of one or more species of activated fatty acid.

In some embodiments, topical compositions of the invention can contain additional ingredients commonly found in skin care compositions and cosmetics, such as for example, tinting agents, emollients, skin conditioning agents, emulsifying agents, humectants, preservatives, antioxidants, perfumes, chelating agents etc., that are compatible with other components of the composition.

As nitroalkenes are very reactive molecules a nitroalkene topical composition desirably includes a substantial antioxidant and preservative system. In one preferred embodiment, the antioxidant system is Oynex™ AP, Oynex™ LM, or Oxynex™ K. The preferred embodiments use fatty acids of Vitamin C, specifically ascorbyl palmitate, as a significant component of the antioxidant system. Antioxidants are typically present in an amount ranging from about 0.025% to about 5.00% by weight of the composition, include, but are not limited to, butylated hydroxy toluene (BHT); vitamin C and/or vitamin C derivatives, such as fatty acid esters of ascorbic acid, particularly ascorbyl palmitate; butylated hydroanisole (BHA); phenyl-a-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the skin such as ascorbyl palmitate. Preservatives are typically present in an amount ranging from about 0.5% to about 2.0% by weight percent, based on the total composition.

Emollients, typically present in amounts ranging from about 0.01% to 5% of the total composition include, but are not limited to, fatty esters, fatty alcohols, mineral oils, polyether siloxane copolymers, and mixtures thereof. Humectants may be present in amounts ranging from about 0.1% to about 5% by weight of the total composition. Non-polar humectants are preferred. Emulsifiers, typically present in amounts from about 1% to about 10% by weight of the composition, include, but are not limited to, stearic acid, cetyl alcohol, stearyl alcohol, steareth 2, steareth 20, acrylates/C10-30 alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof.

Some embodiments of this invention contain at least one other adjunct ingredient in addition to nitroalkene(s). Fat-soluble fatty acid esters of ascorbic acid (vitamin C) are employed as an adjunct ingredient as well as an antioxidant in some embodiments. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one preferred embodiment. Other possible adjunct ingredients include, but are not limited to one or more of: amino acids, lipoic acid; or tocotrienols and tocotrienol derivatives and vitamin E compositions enriched with tocotrienols or tocotrienol derivatives Additional ingredients and methods disclosed in U.S. Pat. Nos. 4,775,530, 5,376,361, 5,409,693, 5,545,398, 5,574,063, 5,643,586, 5,709,868, 5,879,690, 5,965,618, 6,051,244, 6,162,419, and 6,191,121 are hereby incorporated by reference to the extent that they support the present specification.

In particular embodiments, the one or more activated fatty acids may be mixed with one or more stabilizers such as, for example, antioxidants, vitamin E, vitamin C, β-carotene, wheat germ oil and the like, and in some embodiments, the one or more activated fatty acid contained in the composition may be combined with one or more solubilizers such as, for example, surfactants, hydrophilic or hydrophobic solvents, oils or combinations thereof.

For example, in some embodiments a solubilizer may be vitamin E or a vitamin E derivative such as, but not limited to, α-, β-, γ-, δ-, ζ1-, ζ2- and ε-tocopherols, their dl, d and l forms and their structural analogues, such as tocotrienols; the corresponding derivatives, esters, produced with organic acids; and mixtures thereof. In particular embodiments, vitamin E derivative solubilizers may include tocopherols, tocotrienols and tocopherol derivatives with organic acids such as acetic acid, propionic acid, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid, polyethylene glycol succinate and salicylic acid.

In other embodiments, monohydric alcohol including, for example, ethanol, isopropanol, t-butanol, a fatty alcohol, phenol, cresol, benzyl alcohol or a cycloalkyl alcohol, or monohydric alcohol esters of organic acids such as, for example, acetic acid, propionic acid, butyric acid, a fatty acid of 6-22 carbon atoms, bile acid, lactic acid, pyruvic acid, oxalic acid, malic acid, malonic acid, succinic acid, maleic acid, fumaric acid, tartaric acid, citric acid, benzoic acid, cinnamic acid, mandelic acid and salicylic acid may be used as solubilizers. In certain embodiments, solubilizers in this group may include trialkyl citrates such as triethyl citrate, acetyltriethyl citrate, tributyl citrate, acetyltributyl citrate and mixtures thereof; lower alcohol fatty acid esters such as ethyl oleate, ethyl linoleate, ethyl caprylate, ethyl caprate, isopropyl myristate, isopropyl palmitate and mixtures thereof and lactones ε-caprolactone, δ-valerolactone, β-butyrolactone, isomers thereof and mixtures thereof.

In still other embodiments, the solubilizer may be a nitrogen-containing solvent such as, for example, dimethylformamide, dimethylacetamide, N-alkylpyrrolidone, N-hydroxyalkylpyrrolidone, N-alkylpiperidone, N-alkylcaprolactam and mixtures thereof wherein alkyl may be a $C_{1-12}$ branched or straight chain alkyl. In particular embodiments, nitrogen-containing solvents may include N-methyl 2-pyrrolidone, N-ethyl 2-pyrrolidone or a mixture thereof. Alternatively, the nitrogen-containing solvent may be in the form of a polymer such as polyvinylpyrrolidone.

In yet other embodiments, solubilizers may include phospholipids such as phosphatidylcholine, phosphatidylethanolamine, phosphatidylserine, phosphatidylinositol, lecithins, lysolecithins, lysophosphatidylcholine, polyethylene glycolated phospholipids/lisyophospholipids, lecithins/lysolecithins and mixtures thereof.

In still other embodiments, glycerol acetates and acetylated glycerol fatty acid esters and glycerol fatty acid esters may be used as solubilizers. In such embodiments, glycerol acetates may include acetin, diacetin, triacetin and mixtures thereof. Acetylated glycerol fatty acid esters may include acetylated monoglycerides, acetylated diglycerides and mixtures thereof with a fatty acid component that may be about 6 to about 22 carbon atoms. Glycerol fatty acid ester may be a monoglyceride, diglyceride, triglyceride, medium chain monoglycerides with fatty acids having about 6-12 carbons, medium chain diglycerides with fatty acids having about 6-12 carbons, medium chain triglycerides with fatty acids having about 6-12 carbons and mixtures thereof.

Further embodiments include solubilizers that may be a propylene glycol esters or ethylene glycol esters. In such embodiments, propylene glycol esters may include, for example, propylene carbonate, propylene glycol monoacetate, propylene glycol diacetate, propylene glycol fatty acid esters, acetylated propylene glycol fatty acid esters and mixtures thereof. Alternatively, propylene glycol fatty acid esters may be a propylene glycol fatty acid monoester, propylene glycol fatty acid diester or mixture thereof. In certain embodiments, propylene glycol ester may be propylene glycol monocaprylate, propylene glycol dicaprylate, propylene glycol dicaprate, propylene glycol dicaprylate/dicaprate and mixtures thereof. Ethylene glycol esters may include monoethylene glycol monoacetates, diethylene glycol esters, polyethylene glycol esters, ethylene glycol monoacetates, ethylene glycol diacetates, ethylene glycol fatty acid monoesters, ethylene glycol fatty acid diesters, polyethylene glycol fatty acid monoesters, polyethylene glycol fatty acid diesters and mixtures thereof. In such embodiments, the fatty acid may have about 6 to about 22 carbon atoms.

Hydrophilic solvents may also be utilized as solubilizers include, for example, alcohols, for example, water miscible alcohols, such as, ethanol or glycerol; glycols such as 1,2-propylene glycol; polyols such as a polyalkylene glycol, for example, polyethylene glycol. Alternatively, hydrophilic solvents may include N-alkylpyrolidones such as N-methylpyrolidone, triethylcitrate, dimethylisosorbide, caprylic acid or propylene carbonate.

The topical compositions are based on a carrier in which the nitroalkene is soluble per se or is effectively solubilized (e.g. as an emulsion or microemulsion). The carrier is dermatologically acceptable in the sense of not bringing about any adverse effect on the skin areas to which it is applied. The carrier preferably is appropriately selected for topical application, and forms a film or layer on the skin to which it is applied so as to localize the application. The nitroalkene is applied in admixture with the dermatologically acceptable carrier or vehicle (e.g. as a lotion, cream, gel, ointment, soap, stick, or the like) to as to facilitate topical application and provide therapeutic effects.

Non-polar and hydrophobic carriers are required for the compositions of the invention. Aqueous solvents and other polar solvents should be avoided because nitroalkenes are unstable in such solvents. Carriers may include polyethylene glycol, including PEG-1000, PEG-200, PEG-400; PEG-600; Labrasol® (a lipid-based self-emulsifying excipient mainly composed of PEG esters and glycerides with medium acyl chains); glycerin; polypropylene glycol; Stabileze® 06 (a PVM/MA Decadiene Crosspolymer); hydrogenated polyisobutane/polyethane; Permethyl® 99A (isododecane); BV-OSC (tetrahexyldecyl ascorbate); VC-IP (tetrahexyldecyl ascorbate); Vitamine E; beta carotene; disopropyl adipate; 2-ethylhexyl pentate; oleth-3; Ceraphyl® 31 (Propanoic acid 2-hydroxy-dodecyl ester); Ceraphyl® 41 (Propanoic acid, 2-hydroxy-, C12-15-alkyl esters); Glycereth-4; Glycereth-7; diglycerin; panthenol; and phytantriaol. Carrier formulations based principally on polymer polyethers such as polyethylene glycol and polypropylene glycol are a preferred embodiment.

A phosphatidycholine based carrier is another possible embodiment. Phosphatidylcholine, commonly called lecithin, is a mixture of diglycerides of stearic, palmitic, and oleic acids, linked to the choline ester of phosphoric acid. It can be isolated from eggs, soybeans, and other biological materials, chemically synthesized, or obtained commercially from many sources. Carrier formulations as disclosed in U.S. Pat. No. 7,182,956, the disclosure of which is hereby incorporated by reference, including polyenylphosphatidycholine enriched phosphatidycholine and polyglycol mixtures, are particularly preferred.

Additionally, in various embodiments, the activated fatty acid and/or one or more secondary agents of the invention may be formulated with one or more additional non-pharmaceutically active ingredients including, but not limited to, solubilizers, antioxidants, chelating agents, buffers, emulsifiers, thickening agents, dispersants, and preservatives.

Embodiments may also include film forming materials and/or binders and/or other conventional additives such as lubricants, fillers, antiadherents, antioxidants, buffers, solubilizers, dyes, chelating agents, disintegrants, and/or absorption enhancers. Surfactants may act as both solubilizers and absorption enhancers. Additionally, coatings may be formulated for immediate release, delayed or enteric release, or sustained release in accordance with methods well known in the art. Conventional coating techniques are described, e.g., in Remington's Pharmaceutical Sciences, 18th Ed. (1990), hereby incorporated by reference.

In some embodiments, a topical composition may also include one or more preservatives, coloring and opacifying agents, or combinations thereof. Suitable preservatives and colorants are known in the art and include, for example, benzoic acid, para-oxybenzoate, caramel colorant, gardenia colorant, carotene colorant, tar colorant and the like.

In embodiments in which one or more secondary agents are applied in a composition, the secondary agent may be provided as a homogenous solution or a heterologous suspension in a pharmaceutically acceptable solvent. Such pharmaceutically acceptable solvents may be an aqueous or organic solvent such as, for example, methanol, ethanol, isopropanol, ethylene glycol, acetone, or mixtures thereof. In other embodiments, pharmaceutically acceptable solvents may include, but are not limited to, polypropylene glycol; polypropylene glycol; polyethylene glycol, for example, polyethylene glycol 600, polyethylene glycol 900, polyethylene glycol 540, polyethylene glycol 1450, polyethylene glycol 6000, polyethylene glycol 8000, and the like; pharmaceutically acceptable alcohols that are liquids at about room temperature, for example, propylene glycol, ethanol, 2-(2-ethoxyethoxy)ethanol, benzyl alcohol, glycerol, polyethylene glycol 200, polyethylene glycol 300, polyethylene glycol 400 and the like; polyoxyethylene castor oil derivatives, for example, polyoxyethyleneglycerol triricinoleate or polyoxyl 35 castor oil, polyoxyethyleneglycerol oxystearate, RH 40 (polyethyleneglycol 40 hydrogenated castor oil) or RH 60 (polyethyleneglycol 60 hydrogenated castor oil), and the like; saturated polyglycolized glycerides; polyoxyethylene alkyl ethers, for example, cetomacrogol 1000 and the like; polyoxyethylene stearates, for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like; ethyl oleate, isopropyl palmitate, isopropyl myristate and the like; dimethyl isosorbide; N-methylpyrrolidinone; paraffin; cholesterol; lecithin; suppository bases; pharmaceutically acceptable waxes, for example, carnauba wax, yellow wax, white wax, microcrystalline wax, emulsifying wax and the like; pharmaceutically acceptable silicon fluids; sorbitan fatty acid esters such as sorbitan laurate, sorbitan oleate, sorbitan palmitate, sorbitan stearate and the like; pharmaceutically acceptable saturated fats or pharmaceutically acceptable saturated oils, for example, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate and the like.

Other pharmaceutical formulations containing the compounds of the invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Among the acceptable vehicles and solvents that may be employed in a formulation are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, and the like. In some embodiments; the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, caproyl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include activated fatty acid prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of an activated fatty acid in solid dosage form may vary. For example, in one embodiment, a liquid or gelatin formulation of the activated fatty acid may be prepared by combining the activated fatty acid with one or more fatty acid diluent, such as those described above, and adding a thickening agent to the liquid mixture to form a gelatin. The gelatin may then be encapsulated in unit dosage form to form a capsule. In another exemplary embodiment, an oily preparation of an activated fatty acid prepared as described above may be lyophilized to for a solid that may be mixed with one or more pharmaceutically acceptable excipient, carrier or diluent to form a tablet, and in yet another embodiment, the activated fatty acid of an oily preparation may be crystallized to from a solid which may be combined with a pharmaceutically acceptable excipient, carrier or diluent to form a tablet.

Further embodiments which may be useful for oral administration of activated fatty acids include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, activated fatty acids of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids have between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, microgolglyceroli ricinoleas, macrogolglyccroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoxylated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—CH2-CH2-. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to a monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include activated fatty acids administered in combination with other active such as, for example, adjuvants, protease inhibitors, or other compatible drugs or compounds where such combination is seen to be desirable or advantageous in achieving the desired effects of the methods described herein.

Some embodiments are directed to a dietary supplement including a fatty acid component enriched for one or more activated fatty acids fatty acids and a nutraceutically acceptable excipient. In some embodiments, the activated fatty acid may be derived from an omega-3 fatty acid, an omega-6 fatty acid, an omega-9 fatty acid, and combinations thereof. In other embodiments, the activated fatty acid may be a nitro-fatty acid or a keto-fatty acid, and in particular embodiments, the activated fatty acid may be nitro-linoleic acid, nitro-α-linoleic acid, nitro-γ-linoleic acid, nitro-oleic acid, nitro-eicosapentaenoic acid, nitro-docosahexaenoic acid, keto-linoleic acid, keto-α-linoleic acid, keto-γ-linoleic acid, keto-oleic acid, keto-eicosapentaenoic acid, keto-docosahexaenoic acid or a derivative or combination thereof. In still other embodiments, the dietary supplement may also include one or more of linoleic acid, α-linoleic acid, γ-linoleic acid, oleic acid, eicosapentaenoic acid (EPA), docosahexaenoic acid (DHA), or derivatives thereof. DHA and/or nitratel DHA are preferable for cognitive disorders. In some embodiment, the dietary supplement may further include one or more nutraceutical selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof.

In particular embodiments, the dietary supplement may include a first fatty acid component enriched for one or more: activated fatty acid selected from nitro-linoleic acid, keto-linoleic acid, nitro-oleic acid, and keto-oleic acid and a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof, and in some embodiments, the dietary supplement may further include vitamin E or a derivative thereof. In other embodiments, the dietary supplement may include one or more secondary agent including but not limited to vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, gugulipids, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote cognitive health or formulated as a neuroprotectant.

In further embodiments, at least one of the one or more secondary agent may include one or more agents selected from solubilizers, stabilizers, colorants, plasticizers diluents, fillers, disintegrants, binders, lubricants, surfactants, hydrophobic vehicles, water soluble vehicles, emulsifiers, buffers, humectants, moisturizers, antioxidants, or preservatives or a combination thereof.

In certain embodiments, compositions be formulated to include about 10 mg to about 500 mg of one or more activated fatty acid and from about 10 mg to about 100 mg of vitamin C. In other embodiments, such compositions may be formulated to include about 10 mg to about 500 mg of one or more activated fatty acid and from about 2 mg to about 50 mg of vitamin E.

The compositions of various embodiments may further include one or more film forming materials and/or binders and/or other conventional additives such as lubricants, fillers, anti adherents, antioxidants, buffers, solubilizers, dyes, chelating agents, disintegrants, and/or absorption enhancers. Surfactants may act as both solubilizers and absorption enhancers. Additionally, coatings may be formulated for immediate release, delayed or enteric release, or sustained release in accordance with methods well known in the art. Conventional coating techniques are described, e.g., in Remington's Pharmaceutical Sciences, 18th Ed. (1990), hereby incorporated by reference. Additional coatings to be employed in accordance with the invention may include, but are not limited to, for example, one or more immediate release coatings, protective coatings, enteric or delayed release coatings, sustained release coatings, barrier coatings, and combinations thereof. In some embodiments, an immediate release coating may be used to improve product elegance as well as for a moisture barrier, and taste and odor masking. Rapid breakdown of the film in gastric media is important, leading to effective disintegration and dissolution.

In some embodiments, the compositions may include at least one or more secondary agent. For example, in some embodiments, at least one polymer, such as, but not limited to cellulose derivatives such as hydroxyethyl cellulose, hydroxypropyl cellulose, hydroxypropyl methylcellulose, polyvinylpyrrolidone, polyvinylpyrrolidone/vinyl acetate copolymer, ethyl cellulose aqueous dispersions and combinations thereof, preferably hydroxypropyl cellulose, ethyl cellulose, and mixtures thereof, may be added to the composition at a ratio of polymer to secondary agent of from about 1:20 to about 20:1 by weight or about 1:5 to about 10:1 by weight. In particular, where the amount of secondary agent is less than about 15 mg, the amount of polymer may be from about 1:2 to about 5:1 or from about 1:1 to about 4:1, and in embodiments where the amount of secondary agent is about 15 mg or more, the amount of polymer may be from about 1:4 to about 4:1 or about 1:3 to about 2:1.

In embodiments in which one or more secondary agents are included in the composition, the secondary agent may be provided as a homogenous solution or a heterologous suspension in a pharmaceutically acceptable solvent. Such pharmaceutically acceptable solvents may be an aqueous or organic solvent such as, for example, methanol, ethanol, isopropanol, ethylene glycol, acetone, or mixtures thereof. In other embodiments, pharmaceutically acceptable solvents may include, but are not limited to, polypropylene glycol; polypropylene glycol; polyethylene glycol, for example, polyethylene glycol 600, polyethylene glycol 900, polyethylene glycol 540, polyethylene glycol 1450, polyethylene glycol 6000, polyethylene glycol 8000, and the like; pharmaceutically acceptable alcohols that are liquids at about room temperature, for example, propylene glycol, ethanol, 2-(2-ethoxyethoxy)ethanol, benzyl alcohol, glycerol, polyethylene glycol 200, polyethylene glycol 300, polyethylene glycol 400 and the like; polyoxyethylene castor oil derivatives, for example, polyoxyethyleneglycerol triricinoleate or polyoxyl 35 castor oil, polyoxyethyleneglycerol oxystearate, RH 40 (polyethyleneglycol 40 hydrogenated castor oil) or RH 60 (polyethyleneglycol 60 hydrogenated castor oil), and the like; saturated polyglycolized glycerides; polyoxyethylene alkyl ethers, for example, cetomacrogol 1000 and the like; polyoxyethylene stearates, for example, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate and the like; ethyl oleate, isopropyl palmitate, isopropyl myristate and the like; dimethyl isosorbide; N-methylpyrrolidinone; paraffin; cholesterol; lecithin; suppository bases; pharmaceutically acceptable waxes, for example, carnauba wax, yellow wax, white wax, microcrystalline wax, emulsifying wax and the like; pharmaceutically acceptable silicon fluids; sorbitan fatty acid esters such as sorbitan laurate, sorbitan oleate, sorbitan palmitate, sorbitan stearate and the like; pharmaceutically acceptable saturated fats or pharmaceutically acceptable saturated oils, for example, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate and the like.

Other pharmaceutical formulations containing the compounds of the invention and a suitable carrier can be in various forms including, but not limited to, solids, solutions, powders, fluid emulsions, fluid suspensions, semi-solids, and dry powders including an effective amount of an activated fatty acid of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics*, 6th Edition, MacMillan Publishing Co., New York (1980) both of which are hereby incorporated by reference in their entireties can be consulted.

Further embodiments are directed to methods for improving the health of an individual by administering to the individual a dietary supplement including a fatty acid component enriched for one or more activated fatty acids fatty acids, and a nutraceutically acceptable excipient. In some embodiments, the dietary supplement may include a first fatty acid component enriched for one or more activated fatty acid selected from nitro-linoleic acid, keto-linoleic acid, nitro-oleic acid, and keto-oleic acid and a second fatty acid component having one or more non-activated fatty acid selected from linoleic acid, α-linoleic acid, γ-linoleic acid, oleic acid, eicosapentaenoic acid (EPA), docosahexaenoic acid (DHA), or derivatives thereof, and in particular embodiments, the dietary supplement may further include vitamin E or a derivative thereof. In some embodiments, the dietary supplement may further include one or more secondary agent selected from vitamin A, vitamin B, vitamin B-1, vitamin B-2, vitamin B-6, vitamin B-12, vitamin C, vitamin D, vitamin D3, vitamin E, selenium, β-carotene, ginko biloba, goldenseal, valerian, ginseng, echinacea, grape seed extracts, ephedra, yucca concentrates, green tea extract, rice bran extract, wheat germ, wheat germ extract, beeswax, red yeast rice extract, stevia leaf extract, flaxseed oil, borage seed oil, coenzyme Q10, glucosamine derivatives, methylsulfonylmethane, pantothenic acid, biotin, thiamin, riboflavin, niacin, folic acid, palmitic acid, and derivatives thereof. In some embodiments, the dietary supplement may include one or more secondary agent selected from policosanols, guggulipids, rice bran extract, wheat germ, wheat germ extract, beeswax, and red yeast rice extract, and such a dietary supplement may be formulated to promote a healthy heart and circulatory system. In other embodiments, the dietary supplement may include one or more secondary agent selected from vitamin B-1, vitamin B-2, vitamin B-6, vitamin B-12, vitamin C, vitamin D, vitamin D3, vitamin E, selenium, goldenseal, valerian, ginseng, and echinacea and such a dietary supplement may be formulated to promote healthy cell proliferation. In still other embodiments, the dietary supplement may include one or more secondary agent selected from vitamin A, vitamin C, vitamin E, and β-carotene, and such a dietary supplement may be formulated to promote healthy eyes. In yet other embodiments, the dietary supplement may include one or more secondary agent selected from vitamin A, vitamin C, vitamin E, selenium, ginko biloba, goldenseal, valerian, ginseng, echinacea, ephedra, green tea extract, and yucca concentrate, and such a dietary supplement may be formulated to promote cognitive health or formulated as a neuroprotectant.

Various embodiments of the invention are also directed to compositions including one or more nitro fatty acids. In such embodiments, the one or more nitro fatty acids may make up about 10% by weight to about 95% by weight of the total composition. As above, the compositions may include one or more additional secondary components such as, for example, rice bran oil, enzyme-treated stabilized rice bran, a solubilized fraction of rice bran oil, and derivatives thereof, glucosamine derivatives, methylsulfonylmethane, yucca concentrate, grape seed extract, beta-carotene, ephedra, ginko biloba, goldenseal, valerian, ginseng, green tea extract, and echinacea. The activated fatty acid may be derived from an omega-3 fatty acids, omega-6 fatty acids, omega-9 fatty acids, linoleic acid, α-linoleic acid, oleic acid, eicosapentaenoic acid, docosahexaenoic acid or a derivative or combination thereof, and may contain non-activated fatty acids.

In still other embodiments, the core, at least one of the one or more coating layers, or a combination thereof may further include one or more secondary agents such as, for example, antioxidants, statins, squalene synthesis inhibitors, azetidinone-based compounds, low-density lipoprotein (LDL) catabolism activators, peroxisome proliferator-activated receptor (PPAR) antagonists or agonists, antiarrhythmic agent, non-steroidal anti-inflammatory drugs (NSAIDs) and nutraceutical equivalents thereof.

This invention and embodiments illustrating the method and materials used may be further understood by reference to the following non-limiting examples.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Examples 1-9

Exemplary nutraceutical compositions may be prepared as described above including the ingredients listed in Table 1.

| Compound | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| EPA[1] | 0 | 0 | 200 | 100 | 0 | 0 | 0 | 100 | 100 |
| DHA[2] | 400 | 400 | 200 | 300 | 180 | 360 | 14 | 100 | 100 |
| NO-OLA[3] | 0 | 200 | 100 | 0 | 0 | 0 | 0 | 0 | 400 |
| NO-LNA[4] | 200 | 0 | 100 | 200 | 0 | 120 | 240 | 200 | 400 | 0 |
| Vitamin E | 3.0 | 3.0 | 3.0 | 3.0 | 2.3 | 0 | 0 | 3.0 | 3.0 |
| Flavoring | | | | | 1.0 | 1.0 | 2.0 | 1.0 | 1.0 |

[1]EPA—eicosapentaenoic acid
[2]DHA—docosahexaenoic acid
[3]OLA—oleic acid
[4]LNA—linoleic acid Example 10-20

Exemplary nutraceutical compositions may be prepared as described above including the ingredients listed in Table 2.

| Compound | Ex. 10 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| EPA[1] | 200 | 200 | 200 | 200 | 200 | 200 | 200 | 200 | 200 | 200 |
| DHA[2] | 200 | 200 | 200 | 200 | 200 | 200 | 200 | 200 | 200 | 200 |
| NO-OLA[3] | 100 | 100 | 100 | 100 | 100 | 100 | 100 | 100 | 100 | 100 |
| NO-LNA[4] | 100 | 100 | 100 | 100 | 100 | 100 | 100 | 100 | 100 | 100 |
| Vitamin E | 3 | 3 | 3 | 3 | 0 | 0 | 0 | 0 | 0 | 0 |
| Vitamin B12 | 20 | 20 | 0 | 0 | 20 | 20 | 0 | 0 | 0 | 20 |
| Folic Acid | 0 | 0.8 | 0 | 0 | 0 | 0.8 | 0 | 0 | 0 | 0.8 |
| Ginko Biloba | 0 | 0 | 400 | 0 | 0 | 0 | 400 | 0 | 400 | 400 |

-continued

| Compound | Ex. 10 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| Ginseng | 0 | 0 | 0 | 200 | 0 | 0 | 0 | 200 | 200 | 200 |
| Flavoring | 2.0 | 2.0 | 2.0 | 2.0 | 2.0 | 2.0 | 2.0 | 2.0 | 2.0 | 2.0 |

[1]EPA—eicosapentaenoic acid
[2]DHA—docosahexaenoic acid
[3]OLA—oleic acid
[4]LNA—linoleic acid

Example 21

Topical compositions may be prepared including:

0.01% w/w $LNO_2$, 0.01% w/w OA $NO_2$, 2.00 w/w % PEG-400, 2.00% w/w Labrasol, 1.00% w/w Oleth-3, 1.00% w/w Diglycerin, 0.01% w/w Oxynex AP and PEG-200 q.s. to 100% w/w.

0.025% w/w $LNO_2$, 0.01% w/w OA $NO_2$, 5.00 w/w % PEG-400, 2.00% w/w Propylene glycol, 1.00% w/w BV-OSC, 1.00% w/w VC-IP, 0.25% w/w Beta carotene, 5.00% w/w Diisopropyl adipate 0.01% w/w Oxynex AP and PEG-200 q.s. to 100% w/w.

0.02% w/w $LNO_2$, 0.10% w/w Phytantriol, 0.1% w/w Panthenol, 10.00% w/w, 10.00% w/w Glycereth 4, 5.00% w/w Ceraphyl® 41, 1.00% w/w Oleth 3 0.01% w/w Oxynex AP and Diglycerin q.s. to 100% w/w.

Topical emulsion compositions may be prepared including:

0.01% w/w $LNO_2$, 15.00% w/w Ethoxylated glycerin, 5.00% w/w Glycerin, 0.10% w/w NaCl, 1.00% w/w BV-OSC, 35.00% Mineral oil, 2.00% w/w Dow Corning® Fluid 244 (methylsiloxane fluid), 5.00% w/w Abil WE-09 (Polygrycerol-4 isostearate and cetyl dimethicone copolyol and hexyl laureate), 1.00% w/w Cranberry seed oil, 0.01% w/w Oxynex AP and PEG-400 q.s. to 100% w/w.

0.01% w/w OA $NO_2$, 15.00% w/w Ethoxylated glycerin, 5.00% w/w Glycerin, 0.10% w/w NaCl, 1.00% w/w BV-OSC, 35.00% Mineral oil, 2.00% w/w Dow Corning® Fluid 244 (methylsiloxane fluid), 5.00% w/w Abil WE-09 (Polygrycerol-4 isostearate and cetyl dimethicone copolyol and hexyl laureate), 1.00% w/w Cranberry seed oil, 0.01% w/w Oxynex AP and PEG-400 q.s. to 100% w/w.

0.025% w/w $LNO_2$, 5.00% w/w Glycerin, 0.10% w/w NaCl, 1.00% w/w BV-OSC, 35.00% Mineral oil, 2.00% w/w Dow Corning® Fluid 244 (methylsiloxane fluid), 1.00% w/w Cranberry seed oil, 0.01% w/w Oxynex AP and PEG-400 q.s. to 100% w/w.

0.025% w/w OA $NO_2$, 5.00% w/w Glycerin, 0.10% w/w NaCl, 1.00% w/w BV-OSC, 35.00% Mineral oil, 2.00% w/w Dow Corning® Fluid 244 (methylsiloxane fluid), 1.00% w/w Cranberry seed oil, 0.01% w/w Oxynex AP and PEG-400 q.s. to 100% w/w.

0.01% w/w $LNO_2$, 5.00% w/w Glycerin, 0.10% w/w NaCl, 15.00% w/w Dow Corning® Fluid 245 (cyclopentasilxane fluid), 9.00% w/w Dow Corning® Fluid 3225 C (silicone surfactant in dimethylsiloxane), 1.50% w/w Tween 2, 0.01% w/w Oxynex AP and PEG-400 q.s. to 100% w/w.

0.01% w/w OA $NO_2$, 5.00% w/w Glycerin, 0.10% w/w NaCl, 15.00% w/w Dow Corning® Fluid 245 (cyclopentasilxane fluid), 9.00% w/w Dow Corning® Fluid 3225 C (silicone surfactant in dimethylsiloxane), 1.50% w/w Tween 2, 0.01% w/w Oxynex AP and PEG-400 q.s. to 100% w/w.

Topical compositions and emulsions can be applied to areas of the skin such as the face at established intervals resulting in a gradual improvement in the skin areas with each successive application.

Topically applied compositions are absorbed by the skin and can inhibit inflammation. Therefore, topical compositions of the present invention are expected to be particularly useful in the prevention and treatment of conditions including: rosacea, eczema, psoriasis, xerosis, dermatitis (contact and atopic), seborrhea, thermal and radiation burns (including sunburn), acne, alopecia, aging-induced skin tissue degeneration, scars, and other conditions associated with skin inflammation.

It is expected that the compositions of the present invention will also be useful in the treatment and prevention of alopecia, where skin inflammation is frequently present.

Example 22

Stability experiments were conducted using Bertolli extra light olive oil. Methanol soluble impurities were extracted twice. 750 uM OA-$NO_2$ dissolved in methanol was added to the olive oil and incubated for 19 days at 22° C., 37° C. and 50° C. Olive oil is highly hydrophobic and liposomes have been previously shown to stabilize nitrated linoleic acid. The composition of Olive oil used was as follows: total fat: 14 g, saturated fat: 9%, polyunsaturated fat: 9%, Monounsaturated Fat: 45%

First, methanol-soluble substances were extracted from olive oil by applying 6 volumes of methanol per volume of oil and vortexing for a minute. The triglyceride containing fraction was obtained and the extraction was repeated. The remaining triglycerides were dried under vacuum to eliminate remaining organic solvents. Once dry, a concentrated solution of nitrated oleic acid (dissolved in a small volume of ethanol) was added to reach a final concentration of 750 µM. Method of detection.

Samples were then stored in the dark at 22° C., 37° C. and 50° C. A bracketing study for humidity was performed in which the samples at 22° C. and 37° C. were subjected to humidity conditions normally found in the Midwestern United States while the samples at 50° C. were subjected to water-saturated air in an enclosed water bath at 50° C.

At the different time points, aliquot by triplicate were obtained, fatty acids were extracted from the triglyceride matrix using a 4:1 ratio of methanol:triglyceride, diluted to a final concentration of 100 nM and quantified using liquid chromatography coupled to mass spectrometry. The sample (10 µl) was injected using an automated Shimadzu autosampler and HPLC pumps (SIL20 System), and chromatographically separated using a C18 reverse phase column (2 mm Mercury cartridge columns, Phenomenex). The nitrated oleic acid was detected using the multiple reaction monitoring (MRM) process in the negative ion mode performed on a 4000 QTRAP triple quadrupole (Applied Biosystems). The selected MRM corresponded to the formation of the product ion nitrite from the nitrated oleic acid, having a specific transition of 324.3/46. The HPLC method was based on solvent A (H2O with 0.1% Acetic Acid) and B (Acetonitrile with 0.1% Acetic Acid). A gradient was developed starting at 35% B over 6 min to reach 100% B. The column was then washed at 100% B for 2 minutes and re-equilibrated at initial conditions for 3 minutes. The flow rate was established at 750 μl/min. The peak areas were integrated using Analyst 1.5.1 software (Applied Biosystems) and external standard curves were performed for quantification purposes.

FIG. 1 shows stability of 10-nitro oleic acid in olive oil over a period of 19 days at 22° C., 37° C. and 50° C. Stability is plotted as a percentage of the starting concentration of 10-nitro oleic acid. 10-nitro oleic acid is shown to be stable in olive at a range of temperatures for periods of up to 20 days. After 135 days, stability was found to be decreased by about 15% in samples incubated at 22° C., 37° C.

The invention claimed is:

1. A topical composition comprising:
   (i) an activated linoleic acid component selected from the group consisting of nitro-linoleic acid, nitro-α-linoleic acid, nitro-γ-linoleic acid, and combinations thereof;
   (ii) nitro-oleic acid; and
   (iii) a non-activated fatty acid component selected from the group consisting of eicosapentaenoic acid (EPA), docosahexaenoic acid (DHA), linoleic acid, α-linoleic acid, γ-linoleic acid, oleic acid, and combinations thereof; and
   (iv) wherein the weight ratio of the non-activated fatty acid component (iii) to the activated linoleic acid component plus the nitro-oleic acid ((i)+(ii)) is in the range of from about 1:4 to about 4:1; and
   (v) wherein the activated linoleic acid component and the nitro-oleic acid together ((i)+(ii)) are about 5 to about 95 weight percent of the topical composition.

2. The topical composition of claim 1, further comprising a secondary agent selected from the group consisting of antioxidant, statin, squalene synthesis inhibitor, azetidinone-based compound, LDL catabolism activator, PPAR antagonist, PPAR agonist, antiarrhythmic agent, non-steroidal anti-inflammatory agent, steroid, and combinations thereof.

3. The topical composition of claim 1, further comprising a secondary agent selected from the group consisting of hyaluronic acid, chondroitin sulphate, collagen, glucosamine, keratan sulphate, dermatan sulphate, vitamin C, vitamin E, vitamin D, green tea extract, shea butter, grape-seed extract, aloe extract, and combinations thereof.

4. The topical composition of claim 1, further comprising an effective amount of vitamin C.

5. The topical composition of claim 1, further comprising an excipient selected from the group consisting of polypropylene glycol, polyethylene glycol, polyethylene glycol 200, polyethylene glycol 300, polyethylene glycol 400, polyethylene glycol 600, polyethylene glycol 900, polyethylene glycol 540, polyethylene glycol 1450, polyethylene glycol 6000, polyethylene glycol 8000, propylene glycol, ethanol, 2-(2-ethoxyethoxy)ethanol, benzyl alcohol, glycerol, polyoxyethylene castor oil derivatives, polyoxyethyleneglycerol triricinoleate, polyoxyl 35 castor oil, polyoxyethyleneglycerol oxystearate, RH 40 (polyethyleneglycol 40 hydrogenated castor oil), RH 60 (polyethyleneglycol 60 hydrogenated castor oil), saturated polyglycolized glycerides, polyoxyethylene alkyl ethers, cetomacrogol 1000, polyoxyethylene stearates, PEG-6 stearate, PEG-8 stearate, polyoxyl 40 stearate NF, polyoxyethyl 50 stearate NF, PEG-12 stearate, PEG-20 stearate, PEG-100 stearate, PEG-12 distearate, PEG-32 distearate, PEG-150 distearate, ethyl oleate, isopropyl palmitate, isopropyl myristate, dimethyl isosorbide, N-methylpyrrolidinone, paraffin, cholesterol, lecithin, suppository bases, pharmaceutically acceptable waxes, carnauba wax, yellow wax, white wax, microcrystalline wax, emulsifying wax, pharmaceutically acceptable silicon fluids, sorbitan fatty acid esters such as sorbitan laurate, sorbitan oleate, sorbitan palmitate, sorbitan stearate, pharmaceutically acceptable saturated fats or pharmaceutically acceptable saturated oils, hydrogenated castor oil (glyceryl-tris-12-hydroxystearate), cetyl esters wax (a mixture of primarily $C_{14}$-$C_{18}$ saturated esters of $C_{14}$-$C_{18}$ saturated fatty acids having a melting range of about 43-47° C.), glyceryl monostearate, mineral oil, and combinations thereof.

6. The topical composition of claim 1, wherein the topical composition is a salve or lotion.

* * * * *